(12) United States Patent
Eggenweiler et al.

(10) Patent No.: US 8,816,070 B2
(45) Date of Patent: Aug. 26, 2014

(54) TRIAZOLE DERIVATIVE AS AN HSP 90 INHIBITOR

(75) Inventors: Hans Michael Eggenweiler, Darmstadt (DE); Michael Wolf, Darmstadt (DE); Hans Peter Buchstaller, Griesheim (DE); Christian Sirrenberg, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 833 days.

(21) Appl. No.: 12/523,387

(22) PCT Filed: Dec. 11, 2007

(86) PCT No.: PCT/EP2007/010775
§ 371 (c)(1),
(2), (4) Date: Jul. 16, 2009

(87) PCT Pub. No.: WO2008/086857
PCT Pub. Date: Jul. 24, 2008

(65) Prior Publication Data
US 2010/0113542 A1    May 6, 2010

(30) Foreign Application Priority Data
Jan. 18, 2007    (DE) .......................... 10 2007 002 715

(51) Int. Cl.
*A61K 31/4196* (2006.01)
*C07D 249/08* (2006.01)
*C07D 249/12* (2006.01)

(52) U.S. Cl.
CPC .................................. *C07D 249/12* (2013.01)
USPC ........ 544/33; 514/254.05; 514/384; 514/326; 514/383; 548/263.2; 548/269.4; 548/119; 548/264.6; 544/366

(58) Field of Classification Search
CPC ................................................... C07D 249/12
USPC .......... 514/254.05, 384, 326, 383; 548/263.2, 548/269.4, 119, 264.6; 544/33, 366; 536/17.4; 564/102
See application file for complete search history.

(56) References Cited

FOREIGN PATENT DOCUMENTS

WO    WO 2006/087077 A2    8/2006

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
International Search Report of PCT/EP2007/010775 (May 14, 2008).

* cited by examiner

*Primary Examiner* — Savitha Rao
(74) *Attorney, Agent, or Firm* — Millen, White, Zelano & Branigan, P.C.

(57) ABSTRACT

5-[4-(2-Methylphenyl)-3-hydroxy-4H-1,2,4-triazol-5-yl]-2,4-dihydroxy-N-methyl-N-butylbenzamide is an HSP90 inhibitor and can be used for the preparation of a medicament for the treatment of diseases in which the inhibition, regulation and/or modulation of HSP90 plays a role.

7 Claims, 1 Drawing Sheet

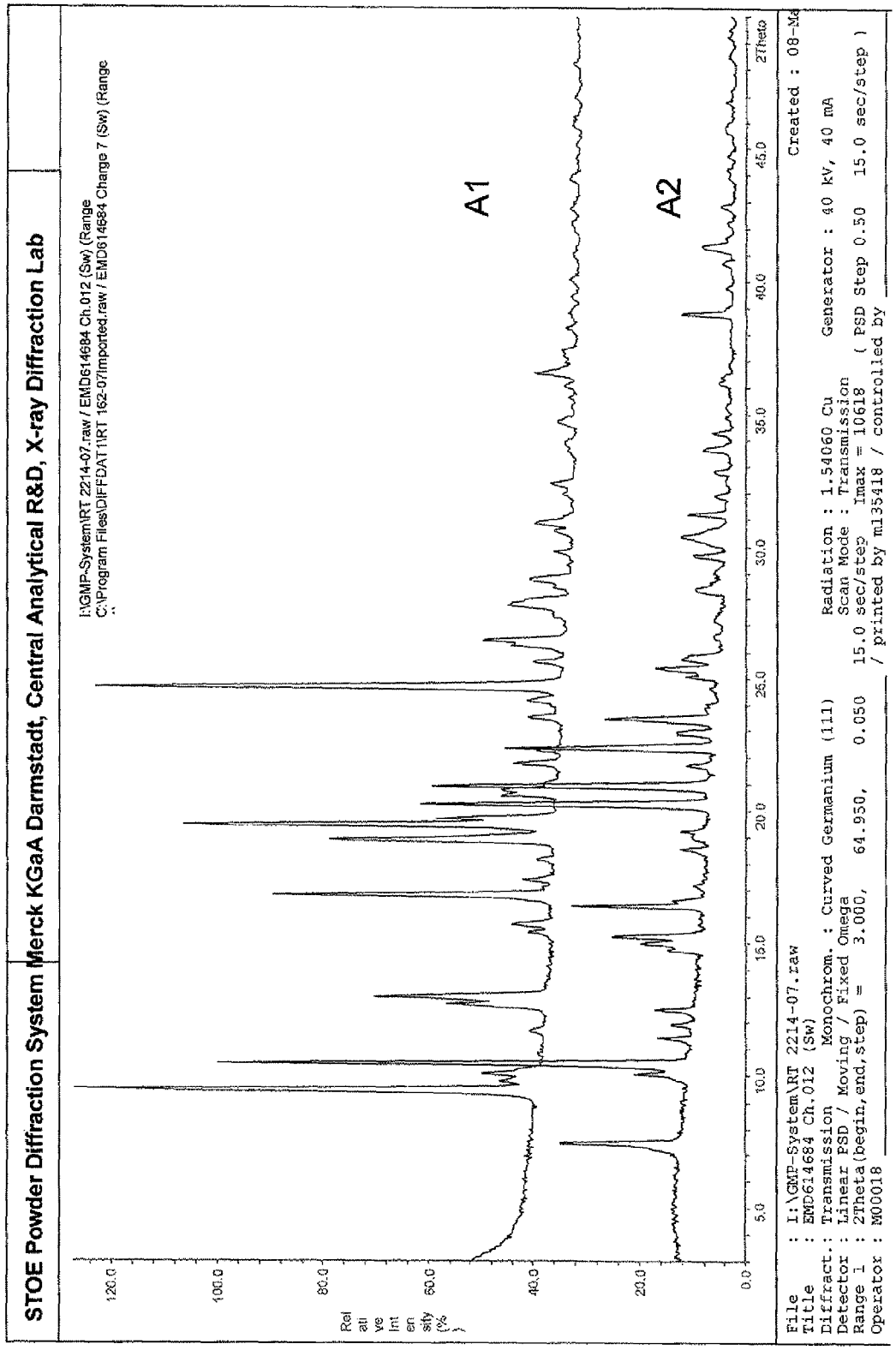

TRIAZOLE DERIVATIVE AS AN HSP 90 INHIBITOR

BACKGROUND OF THE INVENTION

The invention was based on the object of finding novel compounds having valuable properties, in particular those which can be used for the preparation of medicaments.

The present invention relates to a compound in which the inhibition, regulation and/or modulation of HSP90 plays a role, furthermore to pharmaceutical compositions which comprise this compound, and to the use of the compound for the treatment of diseases in which HSP90 plays a role.

The correct folding and conformation of proteins in cells is ensured by molecular chaperones and is critical for the regulation of the equilibrium between protein synthesis and degradation. Chaperones are important for the regulation of many central functions of cells, such as, for example, cell proliferation and apoptosis (Jolly and Morimoto, 2000; Smith et al., 1998; Smith, 2001).

Heat Shock Proteins (HSPs)

The cells of a tissue react to external stress, such as, for example, heat, hypoxia, oxidative stress, or toxic substances, such as heavy metals or alcohols, with activation of a number of chaperones which are known under the term "heat shock proteins" (HSPs).

The activation of HSPs protects the cell against damage initiated by such stress factors, accelerates the restoration of the physiological state and results in a stress-tolerant state of the cell.

Besides this originally discovered protective mechanism promoted by HSPs against external stress, further important chaperone functions have also been described in the course of time for individual HSPs under normal stress-free conditions. Thus, various HSPs regulate, for example, correct folding, intracellular localisation and function or regulated degradation of a number of biologically important proteins of cells.

HSPs form a gene family with individual gene products whose cellular expression, function and localisation differs in different cells. The naming and classification within the family is carried out on the basis of their molecular weight, for example HSP27, HSP70, and HSP90.

Some human diseases are based on incorrect protein folding (see review, for example, Tytell et al., 2001; Smith et al., 1998). The development of therapies which engages in the mechanism of the chaperone-dependent protein folding could therefore be useful in such cases. For example, incorrectly folded proteins result in aggregation of protein with neurodegenerative progression in the case of Alzheimer's disease, prion diseases or Huntington's syndrome. Incorrect protein folding may also result in loss of wild-type function, which can have the consequence of incorrectly regulated molecular and physiological function.

HSPs are also ascribed great importance in tumour diseases. There are, for example, indications that the expression of certain HSPs correlates with the stage of progression of tumours (Martin et al., 2000; Conroy et al., 1996; Kawanishi et al., 1999; Jameel et al., 1992; Hoang et al., 2000; Lebeau et al., 1991).

The fact that HSP90 plays a role in a number of central oncogenic signalling pathways in the cell and certain natural products having cancer-inhibiting activity target HSP90 has led to the concept that inhibition of the function of HSP90 would be sensible in the treatment of tumour diseases. An HSP90 inhibitor, 17-allylamino-17-demethoxygeldanamycin (17AAG), a derivative of geldanamycin, is currently undergoing clinical trials.

HSP90

HSP90 represents approximately 1-2% of the total cellular protein mass. It is usually in the form of a dimer in the cell and is associated with a multiplicity of proteins, so-called co-chaperones (see, for example, Pratt, 1997). HSP90 is essential for the vitality of cells (Young et al., 2001) and plays a key role in the response to cellular stress by interaction with many proteins whose native folding has been modified by external stress, such as, for example, heat shock, in order to restore the original folding or to prevent aggregation of the proteins (Smith et al., 1998).

There are also indications that HSP90 is of importance as buffer against the effects of mutations, presumably through correction of incorrect protein folding caused by the mutation (Rutherford and Lindquist, 1998).

In addition, HSP90 also has a regulatory importance. Under physiological conditions, HSP90, together with its homologue in the endoplasmatic reticulum, GRP94, plays a role in the cell balance for ensuring the stability of the conformation and maturing of various client key proteins. These can be divided into three groups: receptors for steroid hormones, Ser/Thr or tyrosine kinases (for example ERBB2, RAF-1, CDK4 and LCK) and a collection of various proteins, such as, for example, mutated p53 or the catalytic subunit of telomerase hTERT. Each of these proteins takes on a key role in the regulation of physiological and biochemical processes of cells. The preserved HSP90 family in humans consists of four genes, cytosolic HSP90α, the inducible HSP90β isoform (Hickey et al., 1989), GRP94 in the endoplasmatic reticulum (Argon et al., 1999) and HSP75/TRAP1 in the mitochondrial matrix (Felts et al., 2000). It is assumed that all members of the family have a similar mode of action, but, depending on their localisation in the cell, bind to different client proteins. For example, ERBB2 is a specific client protein of GRP94 (Argon et al., 1999), while the type 1 receptor of tumour necrosis factor (TNFR1) or the retinoblastoma protein (Rb) have been found to be clients of TRAP1 (Song et al., 1995; Chen et al., 1996).

HSP90 is involved in a number of complex interactions with a large number of client proteins and regulatory proteins (Smith, 2001). Although precise molecular details have not yet been clarified, biochemical experiments and investigations with the aid of X-ray crystallography in recent years have increasingly been able to decipher details of the chaperone function of HSP90 (Prodromou et al., 1997; Stebbins et al., 1997). Accordingly, HSP90 is an ATP-dependent molecular chaperone (Prodromou et al, 1997), with dimerisation being important for ATP hydrolysis. The binding of ATP results in the formation of a toroidal dimer structure, in which the two N-terminal domains come into close contact with one another and act as a switch in the conformation (Prodromou and Pearl, 2000).

Known HSP90 Inhibitors

The first class of HSP90 inhibitors to be discovered were benzoquinone ansamycins with the compounds herbimycin A and geldanamycin. Originally, the reversion of the malignant phenotype in fibroblasts which had been induced by transformation with the v-Src oncogene was detected with them (Uehara et al., 1985).

Later, a strong antitumoural activity was demonstrated in vitro (Schulte et al., 1998) and in vivo in animal models (Supko et al., 1995).

Immune precipitation and investigations on affinity matrices then showed that the principal mechanism of action of geldanamycin involves binding to HSP90 (Whitesell et al., 1994; Schulte and Neckers, 1998). In addition, X-ray crystallographic studies have shown that geldanamycin competes for the ATP binding site and inhibits the intrinsic ATPase activity of HSP90 (Prodromou et al., 1997; Panaretou et al., 1998). This prevents the formation of the multimeric HSP90 complex, with its property of functioning as chaperone for client proteins. As a consequence, client proteins are degraded via the ubiquitin-proteasome pathway.

The geldanamycin derivative 17-allylamino-17-demethoxygeldanamycin (17AAG) showed an unchanged property in the inhibition of HSP90, the degradation of client proteins and antitumoural activity in cell cultures and in xenograft tumour models (Schulte et al, 1998; Kelland et al, 1999), but had significantly lower liver cytotoxicity than geldanamycin (Page et all 1997). 17AAG is currently undergoing phase I/II clinical trials.

Radicicol, a macrocyclic antibiotic, likewise exhibited revision of the v-Src and v-Ha-Ras-induced malignant phenotype of fibroblasts (Kwon et all 1992; Zhao et al, 1995). Radicicol degrades a large number of signal proteins as a consequence of HSP90 inhibition (Schulte et al., 1998). X-ray crystallographic studies have shown that radicicol likewise binds to the N-terminal domain of HSP90 and inhibits the intrinsic ATPase activity (Roe et al., 1998).

Antibiotics of the coumarine type, as is known, bind to the ATP binding site of the HSP90 homolog DNA gyrase in bacteria. The coumarine, Novobiocin, binds to the carboxy-terminal end of HSP90, i.e. to a different site in HSP90 than the benzoquinone-ansamycins and radicicol, which bind to the N-terminal end of HSP90 (Marcu et al., 2000b).

The inhibition of HSP90 by novobiocin results in degradation of a large number of HSP90-dependent signal proteins (Marcu et al., 2000a).

The degradation of signal proteins, for example ERBB2, was demonstrated using PU3, an HSP90 inhibitor derived from purines. PU3 causes cell cycle arrest and differentiation in breast cancer cell lines (Chiosis et al., 2001).

HSP90 as Therapeutic Target

Due to the participation of HSP90 in the regulation of a large number of signalling pathways which have crucial importance in the phenotype of a tumour, and the discovery that certain natural products exert their biological effect through inhibition of the activity of HSP90, HSP90 is currently being tested as a novel target for the development of a tumour therapeutic agent (Neckers et al., 1999).

The principal mechanism of action of geldanamycin, 17AAG, and radicicol includes the inhibition of the binding of ATP to the ATP binding site at the N-terminal end of the protein and the resultant inhibition of the intrinsic ATPase activity of HSP90 (see, for example, Prodromou et al., 1997; Stebbins et al., 1997; Panaretou et al., 1998). Inhibition of the ATPase activity of HSP90 prevents the recruitment of co-chaperones and favours the formation of an HSP90 hetero-complex, which causes client proteins to undergo degradation via the ubiquitin-proteasome pathway (see, for example, Neckers et al., 1999; Kelland et al., 1999). The treatment of tumour cells with HSP90 inhibitors results in selective degradation of important proteins having fundamental importance for processes such as cell proliferation, regulation of the cell cycle and apoptosis. These processes are frequently deregulated in tumours (see, for example, Hostein et al., 2001). An attractive rationale for the development of an inhibitor of HSP90 is that a strong tumour-therapeutic action can be achieved by simultaneous degradation of a plurality of proteins which are associated with the trans-formed phenotype.

In detail, the present invention relates to a compound which inhibits, regulates and/or modulates HSP90, to compositions which comprise this compound, and to methods for the use thereof for the treatment of HSP90-induced diseases, such as tumour diseases, viral diseases, such as, for example, hepatitis B (Waxman, 2002); immune suppression in transplants (Bijlmakers, 2000 and Yorgin, 2000); inflammation-induced diseases (Bucci, 2000), such as rheumatoid arthritis, asthma, multiple sclerosis, type 1 diabetes, lupus erythematosus, psoriasis and inflammatory bowel disease; cystic fibrosis (Fuller, 2000); diseases associated with angiogenesis (Hur, 2002 and Kurebayashi, 2001), such as, for example, diabetic retinopathy, haemangiomas, endometriosis and tumour angiogenesis; infectious diseases; autoimmune diseases; ischaemia; promotion of nerve regeneration (Rosen et al., WO 02/09696; Degranco et al., WO 99/51223; Gold, U.S. Pat. No. 6,210,974 B1); fibrogenetic diseases, such as, for example, sclerorma, polymyositis, systemic lupus, cirrhosis of the liver, keloid formation, interstitial nephritis and pulmonary fibrosis (Strehlow, WO 02/02123). The invention also relates to the use of the compound according to the invention for the protection of normal cells against toxicity caused by chemotherapy, and to the use in diseases where incorrect protein folding or aggregation is a principal causal factor, such as, for example, scrapie, Creutzfeldt-Jakob disease, Huntington's or Alzheimer's (Sittler, Hum. Mol. Genet., 10, 1307, 2001; Tratzelt et al., Proc. Nat. Acad. Sci., 92, 2944, 1995; Winklhofer et al., J. Biol. Chem., 276, 45160, 2001). WO 01/72779 describes purine compounds and the use thereof for the treatment of GRP94 (homologue or paralogue of HSP90)-induced diseases, such as tumour diseases, where the cancerous tissue includes a sarcoma or carcinoma selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous gland carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, smallcell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenström's macroglobulinaemia and heavy chain disease.

A. Kamal et al. in Trends in Molecular Medicine, Vol. 10 No. 6 Jun. 2004, describe therapeutic and diagnostic applications of HSP90 activation, inter alia for the treatment of diseases of the central nervous system and of cardiovascular diseases.

The identification of small compounds which specifically inhibit, regulate and/or modulate HSP90 is therefore desirable and an aim of the present invention.

It has been found that 5-[4-(2-methylphenyl)-3-hydroxy-4H-1,2,4-triazol-5-yl]-2,4-dihydroxy-N-methyl-N-butyl-benzamide and salts thereof have very valuable pharmacological properties while being well tolerated. In particular, it exhibits HSP90-inhibiting properties.

The present invention therefore relates to 5-[4-(2-methylphenyl)-3-hydroxy-4H-1,2,4-triazol-5-yl]-2,4-dihydroxy-N-methyl-N-butylbenzamide as medicament and/or medicament active ingredient in the treatment and/or prophylaxis of the said diseases and to the use of 5-[4-(2-methylphenyl)-3- hydroxy-4H-1,2,4-triazol-5-yl]-2,4-dihydroxy-N-methyl-N-butylbenzamide for the preparation of a pharmaceutical for the treatment and/or prophylaxis of the said diseases and also to a process for the treatment of the said diseases which comprises the administration of 5-[4-(2-methylphenyl)-3-hydroxy-4H-1,2,4-triazol-5-yl]-2,4-dihydroxy-N-methyl-N-butylbenzamide to a patient in need of such an administration.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

PRIOR ART

WO 2006/087077 describes other triazole derivatives as HSP90 inhibitors. The present invention should be regarded as a selection invention hereto. The closest prior art that should be mentioned therefrom is the compound 5-[4-(2-methylphenyl)-3-hydroxy-4H-1,2,4-triazol-5-yl]-2,4-dihydroxy-N-methyl-N-propylbenzamide ("A47").

WO 00/53169 describes HSP90 inhibition with coumarine or a coumarine derivative.

WO 03/041643 A2 discloses HSP90-inhibiting zearalanol derivatives. HSP90-inhibiting pyrazole derivatives which are substituted by an aromatic radical in the 3- or 5-position are disclosed in WO 2004/050087 A1 and WO 2004/056782 A1.

WO 03/055860 A1 describes 3,4-diarylpyrazoles as HSP90 inhibitors. Purine derivatives having HSP90-inhibiting properties are disclosed in WO 02/36075 A2.

WO 01/72779 describes purine compounds and the use thereof for the treatment of GRP94 (homologue or paralogue of HSP90)-induced diseases, such as tumour diseases, where the cancerous tissue includes a sarcoma or carcinoma selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous gland carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenström's macroglobulinaemia and heavy chain disease.

WO 01/72779 furthermore discloses the use of the compounds mentioned therein for the treatment of viral diseases, where the viral pathogen is selected from the group consisting of hepatitis type A, hepatitis type B, hepatitis type C, influenza, varicella, adenovirus, herpes simplex type I (HSV-I), herpes simplex type II (HSV-II), cattle plague, rhinovirus, echovirus, rotavirus, respiratory syncytial virus (RSV), papillomavirus, papovavirus, cytomegalovirus, equinovirus, arbovirus, huntavirus, Coxsackie virus, mumps virus, measles virus, rubella virus, polio virus, human immunodeficiency virus type I (HIV-I) and human immunodeficiency virus type II (HIV-II). WO 01/72779 furthermore describes the use of the compounds mentioned therein for GRP94 modulation, where the modulated biological GRP94 activity causes an immune reaction in an individual, protein transport from the endoplasmatic reticulum, recovery from hypoxic/anoxic stress, recovery from malnutrition, recovery from heat stress, or combinations thereof, and/or where the disorder is a type of cancer, an infectious disease, a disorder associated with disrupted protein transport from the endoplasmatic reticulum, a disorder associated with ischaemia/reperfusion, or combinations thereof, where the disorder associated with ischaemia/reperfusion is a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

Finally, WO 01/72779 describes the use of an effective amount of a GRP94 protein modulator for the preparation of a medicament for changing a subsequent cellular reaction to an ischaemic state in a tissue site in an individual, by treatment of the cells at the tissue site with the GRP94 protein modulator in order that the GRP94 activity in cells is increased to such an extent that a subsequent cellular reaction to an ischaemic state is changed, where the subsequent ischaemic condition is preferably the consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress, or where the tissue site is the donor tissue for a transplant.

The specifications mentioned below describe combinations of the HSP90 inhibitor geldanamycin with other medicament active ingredients:

WO 2004/108080 A2, WO 2005/002506 A2, WO 2005/000211 A2, WO 2005/000212 A2, WO 2005/000213 A2, WO 2005/000214 A2, WO 2005/000314 A1.

Further Literature

Argon Y and Simen B B. 1999 "Grp94, an ER chaperone with protein and peptide binding properties", Semin. Cell Dev. Biol., Vol. 10, pp. 495-505.

Bijlmakers M-J J E, Marsh M. 2000 "Hsp90 is essential for the synthesis and subsequent membrane association, but not the maintenance, of the Src-kinase p56Ick", Mol. Biol. Cell, Vol. 11(5), pp. 1585-1595.

Bucci M; Roviezzo F; Cicala C; Sessa W C, Cirino G. 2000 "Geldanamycin, an inhibitor of heat shock protein 90 (Hsp90) mediated signal transduction has anti-inflammatory effects and interacts with glucocorticoid receptor in vivo", Brit. J. Pharmacol., Vol. 131(1), pp. 13-16.

Carreras C W, Schirmer A, Zhong Z, Santi V S. 2003 "Filter binding assay for the geldanamycin-heat shock protein 90 interaction", Analytical Biochem., Vol. 317, pp 40-46.

Chen C-F, Chen Y, Dai K D, Chen P-L, Riley D J and Lee W-H. 1996 "A new member of the hsp90 family of molecular chaperones interacts with the retinoblastoma protein during mitosis and after heat shock", Mol. Cell. Biol., Vol. 16, pp. 4691-4699.

Chiosis G, Timaul M N, Lucas B, Munster P N, Zheng F F, Sepp-Lozenzino L and Rosen N. 2001 "A small molecule designed to bind to the adenine nucleotide pocket of HSP90 causes Her2 degradation and the growth arrest and differentiation of breast cancer cells", Chem. Biol., Vol. 8, pp. 289-299.

Chiosis G, Lucas B, Shtil A, Huezo H, Rosen N 2002 "Development of a purine-scaffold novel class of HSP90 binders that inhibit the proliferation of cancer cells and induce the degradation of her2 tyrosine kinase". Bioorganic Med. Chem., Vol. 10, pp 3555-3564.

Conroy S E and Latchman D S. 1996 "Do heat shock proteins have a role in breast cancer?", Brit. J. Cancer, Vol. 74, pp. 717-721. Felts S J, Owen B A L, Nguyen P, Trepel J, Donner D B and Toft D O. 2000 "The HSP90-related protein TRAP1 is a mitochondrial protein with distinct functional properties", J. Biol. Chem., Vol. 5, pp. 3305-3312.

Fuller W, Cuthbert A W. 2000 "Post-translational disruption of the delta F508 cystic fibrosis transmembrane conductance regulator (CFTR)-molecular Chaperone complex with geldanamycin stabilises delta F508 CFTR in the rabbit reticulocyte lysate", J. Biol. Chem., Vol. 275(48), pp. 37462-37468.

Hickey E, Brandon S E, Smale G, Lloyd D and Weber L A. 1999 "Sequence and regulation of a gene encoding a human 89-kilodalton heat shock protein", Mol. Cell. Biol., Vol. 9, pp. 2615-2626.

Hoang A T, Huang J, Rudra-Gonguly N, Zheng J, Powell W C, Rabindron S K, Wu C and Roy-Burman P. 2000 "A novel association between the human heat shock transcription factor 1 (HSF1) and prostate adenocarcinoma, Am. J. Pathol., Vol. 156, pp. 857-864.

Hostein I, Robertson D, Di Stefano F, Workman P and Clarke P A. 2001 "Inhibition of signal transduction by the HSP90 inhibitor 17-allylamino-17-demethoxygeldanamycin results in cytostasis and apoptosis", Cancer Res., Vol. 61, pp. 4003-4009.

Hur E, Kim H-H, Choi S M, Kim J H, Yim S, Kwon H J, Choi Y, Kim D K, Lee M-0, Park H. 2002 "Reduction of hypoxia-induced transcription through the repression of hypoxia-inducible factor-1α/aryl hydrocarbon receptor nuclear translocator DNA binding by the 90-kDa heat-shock protein inhibifor radicicol", Mol. Pharmacol., Vol. 62(5), pp. 975-982.

Jameel A, Skilton R A, Campbell T A, Chander S K, Coombes R C and Luqmani Y A. 1992 "Clinical and biological significance of HSP89 alpha in human cancer, "Int J Cancer, Feb 1;50(3);409-15.

Jolly C and Morimoto R I. 2000 "Role of the heat shock response and molecular chaperones in oncogenesis and cell death", J. Natl. Cancer Inst., Vol. 92, pp. 1564-1572.

Kawanishi K, Shiozaki H, Doki Y, Sakita I, Inoue M, Yano M, Tsujinata T, Shamma A and Monden M. 1999 "Prognostic significance of heat shock proteins 27 and 70 in patients with squamous cell carcinoma of the esophagus", Cancer, Vol. 85, pp. 1649-1657.

Kelland L R, Abel G, McKeage M J, Jones M, Goddard P M, Valenti M, Murrer B A, and Harrap K R. 1993 "Preclinical antitumour evaluation of bisacetalo-amino-dichloro-cyclohexylamine platinum (IV): an orally active platinum drug", Cancer Research, Vol. 53, pp. 2581-2586.

Kelland L R, Sharp S Y, Rogers P M, Myers T G and Workman P. 1999 "DT-diaphorase expression and tumor cell sensitivity to 17-allylamino, 17-demethoxygeldanamycin, an inhibitor of heat shock protein 90", J. Natl. Cancer Inst., Vol. 91, pp. 1940-1949.

Kurebayashi J, Otsuki T, Kurosumi M, Soga S, Akinaga S, Sonoo, H. 2001 "A radicicol derivative, KF58333, inhibits expression of hypoxia-inducible factor-1α and vascular endothelial growth factor, angiogenesis and growth of human breast cancer xenografts", Jap. J. Cancer Res., Vol. 92(12), 1342-1351.

Kwon H J, Yoshida M, Abe K, Horinouchi S and Bepple T. 1992 "Radicicol, an agent inducing the reversal of transformed phenotype of src-trans-formed fibroblasts, Biosci., Biotechnol., Biochem., Vol. 56, pp. 538-539. Lebeau J, Le Cholony C, Prosperi M T and Goubin G. 1991 "Constitutive overexpression of 89 kDa heat shock protein gene in the HBL100 mammary cell line converted to a tumorigenic phenotype by the EJE24 Harvey-ras oncogene", Oncogene, Vol. 6, pp. 1125-1132.

Marcu M G, Chadli A, Bouhouche I, Catelli M and Neckers L. 2000a "The heat shock protein 90 antagonist novobiocin interacts with a previously unrecognised ATP-binding domain in the carboxyl terminus of the chaperone", J. Biol. Chem., Vol. 275, pp. 37181-37186.

Marcu M G, Schulte T W and Neckers L. 2000b "Novobiocin and related coumarins and depletion of heat shock protein 90-dependent signaling proteins", J. Natl. Cancer Inst., Vol. 92, pp. 242-248.

Martin K J, Kritzman B M, Price L M, Koh B, Kwan C P, Zhang X, MacKay A, O'Hare M J, Kaelin C M, Mutter G L, Pardee A B and Sager R. 2000 "Linking gene expression patterns to therapeutic groups in breast cancer", Cancer Res., Vol. 60, pp. 2232-2238.

Neckers L, Schulte T W and Momnaaugh E. 1999 "Geldanamycin as a potential anti-cancer agent: its molecular target and biochemical activity", Invest. New Drugs, Vol. 17, pp. 361-373.

Page J, Heath J, Fulton R, Yalkowsky E, Tabibi E, Tomaszewski J, Smith A and Rodman L. 1997 "Comparison of geldanamycin (NSC-122750) and 17-allylaminogeldanamycin (NSC-330507D) toxicity in rats", Proc. Am. Assoc. Cancer Res., Vol. 38, pp. 308.

Panaretou B, Prodromou C, Roe S M, OBrien R, Ladbury J E, Piper P W and Pearl L H. 1998 "ATP binding and hydrolysis are essential to the function of the HSP90 molecular chaperone in vivo", EMBO J., Vol. 17, pp. 4829-4836.

Pratt W B. 1997 "The role of the HSP90-based chaperone system in signal transduction by nuclear receptors and receptors signalling via MAP kinase", Annu. Rev. Pharmacol. Toxicol., Vol. 37, pp. 297-326.

Prodromou C, Roe S M, O'Brien R, Ladbury J E, Piper P W and Pearl L H. 1997 "Identification and structural characterisation of the ATP/ADP-binding site in the HSP90 molecular chaperone", Cell, Vol. 90, pp. 65-75.

Prodromou C, Panaretou B, Chohan S, Siligardi G, O'Brien R, Ladbury J E, Roe S M, Piper P W and Pearl L H. 2000 "The ATPase cycle of HSP90 drives a molecular "clamp" via transient dimerisation of the N-terminal domains", EMBO J., Vol. 19, pp. 4383-4392.

Roe S M, Prodromou C, O'Brien R, Ladbury J E, Piper P W and Pearl L H. 1999 "Structural basis for inhibition of the HSP90 molecular chaperone by the antitumour antibiotics radicicol and geldanamycin", J. Med. Chem., Vol. 42, pp. 260-266.

Rutherford S L and Lindquist S. 1998 "HSP90 as a capacitor for morphological evolution. Nature, Vol. 396, pp. 336-342.

Schulte T W, Akinaga S, Murakata T, Agatsuma T, Sugimoto S, Nakano H, Lee Y S, Simen B B, Argon Y, Felts S, Toft D O, Neckers L M and Sharma S V. 1999 "Interaction of radicicol with members of the heat shock protein 90 family of molecular chaperones", Mol. Endocrinology, Vol. 13, pp. 1435-1448.

Schulte T W, Akinaga S, Soga S, Sullivan W, Sensgard B, Toft D and Neckers L M. 1998 "Antibiotic radicicol binds to the N-terminal domain of HSP90 and shares important biologic activities with geldanamcyin", Cell Stress and Chaperones, Vol. 3, pp. 100-108.

Schulte T W and Neckers L M. 1998 "The benzoquinone ansamycin 17-allylamino-17-demethoxygeldanamcyin binds to HSP90 and shares important biologic activities with geldanamycin", Cancer Chemother. Pharmacol., Vol. 42, pp. 273-279.

Smith D F. 2001 "Chaperones in signal transduction", in: Molecular chaperones in the cell (P Lund, ed.; Oxford University Press, Oxford and NY), pp. 165-178.

Smith D F, Whitesell L and Katsanis E. 1998 "Molecular chaperones: Biology and prospects for pharmacological intervention", Pharmacological Reviews, Vol. 50, pp. 493-513.

Song H Y, Dunbar J D, Zhang Y X, Guo D and Donner D B. 1995 "Identification of a protein with homology to hsp90 that binds the type 1 tumour necrosis factor receptor", J. Biol. Chem., Vol. 270, pp. 3574-3581.

Stebbins C E, Russo A, Schneider C, Rosen N, Hartl F U and Pavletich N P. 1997 "Crystal structure of an HSP90-geldanamcyin complex: targeting of a protein chaperone by an antitumor agent", Cell, Vol. 89, pp. 239-250.

Supko J G, Hickman R L, Grever M R and Malspeis L. 1995 "Preclinical pharmacologic evaluation of geldanamycin as an antitumour agent", Cancer Chemother. Pharmacol., Vol. 36, pp. 305-315.

Tytell M and Hooper P L. 2001 "Heat shock proteins: new keys to the development of cytoprotective therapies", Emerging Therapeutic Targets, Vol. 5, pp. 267-287.

Uehara U, Hori M, Takeuchi T and Umezawa H. 1986 "Phenotypic change from transformed to normal induced by benzoquinoid ansamycins accompanies inactivation of p60src in rat kidney cells infected with Rous sarcoma virus", Mol. Cell. Biol., Vol. 6, pp. 21 98-2206.

Waxman, Lloyd H. Inhibiting hepatitis C virus processing and replication. (Merck & Co., Inc., USA). PCT Int. Appl. (2002), WO 0207761 Whitesell L, Mimnaugh E G, De Costa B, Myers C E and Neckers L M. 1994 "Inhibition of heat shock protein HSP90-pp 60v-src heteroprotein complex formation by benzoquinone ansamycins: essential role for stress proteins in oncogenic transformation", Proc. Natl. Acad. Sci. USA., Vol. 91, pp. 8324-8328.

Yorgin et al. 2000 "Effects of geldanamycin, a heat-shock protein 90-binding agent, on T cell function and T cell nonreceptor protein tyrosine kinases", J. Immunol., Vol. 164(6), pp. 2915-2923.

Young J C, Moarefi I and Hartl F U. 2001 "HSP90: a specialised but essential protein-folding tool", J. Cell. Biol., Vol. 154, pp. 267-273.

Zhao J F, Nakano H and Sharma S. 1995 "Suppression of RAS and MOS transformation by radicicol", Oncogene, Vol. 11, pp. 161-173.

SUMMARY OF THE INVENTION

The invention relates to the compound 5-[4-(2-methylphenyl)-3-hydroxy-4H-1,2,4-triazol-5-yl]-2,4-dihydroxy-N-methyl-N-butylbenzamide and pharmaceutically usable derivatives, salts, solvates, tautomers and stereoisomers thereof, including mixtures thereof in all ratios.

In particular, the invention relates to the compound 5-[4-(2-methylphenyl)-3-hydroxy-4H-1,2,4-triazol-5-yl]-2,4-dihydroxy-N-methyl-N-butylbenzamide and pharmaceutically usable derivatives, tautomers and stereoisomers thereof, including mixtures thereof in all ratios.

The invention particularly preferably relates to the compound 5-[4-(2-methylphenyl)-3-hydroxy-4H-1,2,4-triazol-5-yl]-2,4-dihydroxy-N-methyl-N-butylbenzamide and mono- and diphosphoric acid derivatives, thioxoderivatives, mono- and diglucuronic acid derivatives, tautomers and stereoisomers thereof, including mixtures thereof in all ratios.

The invention very particularly preferably relates to the compound 5-[4-(2-methylphenyl)-3-hydroxy-4H-1,2,4-triazol-5-yl]-2,4-dihydroxy-N-methyl-N-butylbenzamide.

The invention also relates to the hydrates and solvates of these compounds. solvates of the compounds are taken to mean adductions of inert solvent molecules onto the compounds which form owing to their mutual attractive force. solvates are, for example, mono- or dihydrates or alcoholates.

The compound according to the invention may also exist in the following tautomeric form

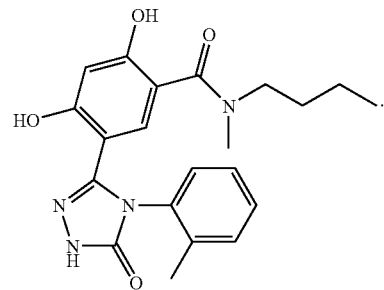 [SMILES: CCCCN(C)C(=O)c1cc(-c2n[nH]c(=O)n2-c2ccccc2C)c(O)cc1O]

Pharmaceutically usable derivatives are taken to mean, for example, the salts of the compound according to the invention and also so-called prodrug compounds.

Prodrug derivatives are taken to mean the compound according to the invention which has been modified with, for example, alkyl or acyl groups, sugars or oligopeptides and which is rapidly cleaved in the organism to give the active compound according to the invention.

These also include biodegradable polymer derivatives of the compound according to the invention, as described, for example, in Int. J. Pharm. 115, 61-67 (1995).

Particularly preferred prodrugs are the phosphoric acid ester derivatives, such as, for example, the mono- and/or diphosphoric acid ester derivatives; sugar derivatives, such as, for example, the mono- and/or diglucuronides or the 5-thioxo derivatives.

The expression "effective amount" means the amount of a medicament or pharmaceutical active ingredient which causes a biological or medical response which is sought or desired, for example, by a researcher or physician in a tissue, system, animal or human.

In addition, the expression "therapeutically effective amount" means an amount which, compared with a corresponding subject who has not received this amount, has the following consequence:

improved healing treatment, healing, prevention or elimination of a disease, a disease picture, a disease state, a complaint, a disorder or of side effects or also the reduction in the progress of a disease, a complaint or a disorder.

The term "therapeutically effective amount" also encompasses the amounts which are effective for increasing normal physiological function.

The invention also relates to mixtures of the compound according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The compound according to the invention and also the starting materials for its preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds according to the invention.

The starting compounds are generally known. If they are novel, however, they can be prepared by methods known per se.

The compound according to the invention is prepared by methods as described in WO 2006/087077.

The reaction is carried out by methods which are known to the person skilled in the art.

The reaction is carried out in a suitable inert solvent.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The solvent is particularly preferably, for example, tetrahydrofuran.

Depending on the conditions used, the reaction time is between a few minutes and 14 days, the reaction temperature is between about −30° and 140°, normally between −10° and 130°, in particular between about 30° and about 125°.

The protecting groups are removed by methods which are known to the person skilled in the art.

The cleavage of an ether, for example a methyl ether, is carried out in a suitable solvent, as indicated above, preferably by addition of boron tribromide.

The reaction is particularly preferably carried out in dichloromethane at a reaction temperature between about −30° and 50°, normally between −20° and 20°, in particular between about −15° and about 0°.

The compound according to the invention can furthermore be obtained by liberating them from functional derivatives thereof by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula I, but contain an NHR' group (in which R' denotes an amino-protecting group, for example BOC or CBZ) instead of an $NH_2$ group.

Preference is furthermore given to starting materials which carry a hydroxyl-protecting group instead of the H atom of an hydroxyl group, for example those which conform to the formula I, but contain an R"O-phenyl group (in which R" denotes an hydroxyl-protecting group) instead of an hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf or Pmc. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, p-nitrobenzoyl, p-toluenesulfonyl, tert-butyl and acetyl, where benzyl and tert-butyl are particularly preferred. COOH groups are preferably protected in the form of their tert-butyl esters.

The compound according to the invention is liberated from its functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

Protecting groups which can be removed hydrogenolytically (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts And Other Forms

The said compound according to the invention can be used in its final non-salt form. On the other hand, the present invention also encompasses the use of this compound in the form of its pharmaceutically acceptable salts, which can be derived from various organic and inorganic acids and bases by procedures known in the art. Pharmaceutically acceptable salt forms of the compound according to the invention are for the most part prepared by conventional methods. A suitable salt can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compound according to the invention are likewise included. Acid-addition salts can also be formed by treating the compound with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compound according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compound according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compound according to the invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

The compound according to the invention of the present invention which contain basic nitrogen-containing groups can be quaternised using agents such as ($C_1$-$C_4$)alkyl halides, for example methyl, ethyl, isopropyl and tertbutyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of the compound according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compound according to the invention are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

With regard to that stated above, it can be seen that the expression "pharmaceutically acceptable salt" in the present connection is taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to the use of the compound according to the invention and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising 5-[4-(2-methylphenyl)-3-hydroxy-4H-1,2,4-triazol-5-yl]-2,4-dihydroxy-N-methyl-N-butylbenzamide and/or pharmaceutically usable derivatives, salts, solvates, tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.1 mg to 3 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or drypressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compound according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compounds. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compound according to the invention and/or pharmaceutically usable derivatives, salts, solvates, tautomers and stereoisomers thereof, including mixtures thereof in all ratios, and optionally excipients and/or adjuvants and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compound according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of the compound according to the invention depends on a number of factors, including, for example, the age and weight of the human or animal, the precise disease condition which requires treatment, and its severity, the nature of the formulation and the method of administration, and is ultimately determined by the treating doctor or vet. However, an effective amount of the compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active ingredient.

Further medicament active ingredients are preferably chemotherapeutic agents, in particular those which inhibit angiogenesis and thus inhibit the growth and spread of tumour cells; preference is given here to VEGF receptor inhibitors, including robozymes and antisense which are directed to VEGF receptors, and angiostatin and endostatin.

Examples of antineoplastic agents which can be used in combination with the compounds according to the invention generally include alkylating agents, antimetabolites; epidophyllotoxin; an antineoplastic enzyme; a topoisomerase inhibitor; procarbazin; mitoxantron or platinum coordination complexes.

Antineoplastic agents are preferably selected from the following classes: anthracyclins, vinca medicaments, mitomycins, bleomycins, cytotoxic nucleosides, epothilones, discormolides, pteridines, diynenes and podophyllotoxins.

Particular preference is given in the said classes to, for example, caminomycin, daunorubicin, aminopterin, methotrexate, methopterin, dichloromethotrexate, mitomycin C, porfiromycin, 5-fluorouracil, 5-fluorodeoxyuridine monophosphate, cytarabine, 5-azacytidine, thioguanine, azathioprine, adenosine, pentostatin, erythrohydroxynonyladenine, cladribine, 6-mercaptopurine, gemcitabine, cytosinarabinoside, podophyllotoxin or podophyllotoxin derivatives, such as, for example, etoposide, etoposide phosphate or teniposide, melphalan, vinblastine, vinorelbine, vincristine, leurosidine, vindesine, leurosine, docetaxel and paclitaxel. Other preferred antineoplastic agents are selected from the group discormolide, epothilone D, estramustine, carboplatin, cisplatin, oxaliplatin, cyclophosphamide, bleomycin, gemcitabine, ifosamide, melphalan, hexamethylmelamine, thiotepa, idatrexate, trimetrexate, dacarbazine, L-asparaginase, camptothecin, CPT-11, topotecan, arabinosylcytosine, bicalutamide, flutamide, leuprolide, pyridobenzoindole derivatives, interferons and interleukins.

Further medicament active ingredients are preferably antibiotics. Preferred antibiotics are selected from the group
dactinomycin, daunorubicin, idarubicin, epirubicin, mitoxantrone, bleomycin, plicamycin, mitomycin.

Further medicament active ingredients are preferably enzyme inhibitors. Preferred enzyme inhibitors are selected from the group
of the histone deacetylation inhibitors (for example suberoylanilide hydroxyamic acid [SAHA]) and the tyrosine kinase inhibitors (for example ZD 1839 [Iressa]).

Further medicament active ingredients are preferably nuclear export inhibitors. Nuclear export inhibitors prevent the output of biopolymers (for example RNA) from the cell nucleus. Preferred nuclear export inhibitors are selected from the group callystatin, leptomycin B, ratjadone.

Further medicament active ingredients are preferably nuclear export inhibitors. Nuclear export inhibitors prevent the output of biopolymers (for example RNA) from the cell nucleus. Preferred nuclear export inhibitors are selected from the group callystatin, leptomycin B, ratjadone.

Further medicament active ingredients are preferably immunosuppressants. Preferred immunosuppressants are selected from the group rapamycin, CCl-779 (Wyeth), RAD001 (Novartis), AP23573 (Ariad Pharmaceuticals).

The invention also relates to a set (kit) consisting of separate packs of
(a) an effective amount of the compound according to the invention and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Use

The present compound is suitable as pharmaceutical active ingredient for mammals, in particular for humans, in the treatment of diseases in which HSP90 plays a role.

The invention thus relates to the use of 5-[4-(2-methylphenyl)-3-hydroxy-4H-1,2,4-triazol-5-yl]-2,4-dihydroxy-N-methyl-N-butylbenzamide, and pharmaceutically usable derivatives, solvates and stereoisomers thereof, including mixtures thereof in all ratios, for the preparation of a medicament for the treatment of diseases in which the inhibition, regulation and/or modulation of HSP90 plays a role.

The present invention encompasses the use of 5-[4-(2-methylphenyl)-3-hydroxy-4H-1,2,4-triazol-5-yl]-2,4-dihydroxy-N-methyl-N-butylbenzamide and pharmaceutically usable derivatives, solvates and stereoisomers thereof, including mixtures thereof in all ratios, for the preparation of a medicament for the treatment of tumour diseases, for example fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous gland carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenström's macroglobulinaemia and heavy chain disease;

viral diseases, where the viral pathogen is selected from the group consisting of hepatitis type A, hepatitis type B, hepatitis type C, influenza, varicella, adenovirus, herpes simplex type I (HSV-I), herpes simplex type II (HSV-II), cattle plague, rhinovirus, echovirus, rotavirus, respiratory syncytial virus (RSV), papillomavirus, papovavirus, cytomegalovirus, echinovirus, arbovirus, huntavirus, Coxsackie virus, mumps virus, measles virus, rubella virus, polio virus, human immunodeficiency virus type I (HIV-I) and human immunodeficiency virus type II (HIV-II);

for immune suppression in transplants; inflammation-induced diseases, such as rheumatoid arthritis, asthma, multiple sclerosis, type 1 diabetes, lupus erythematosus, psoriasis and inflammatory bowel disease; cystic fibrosis; diseases associated with angiogenesis, such as, for example, diabetic retinopathy, haemangioma, endometriosis, tumour angiogenesis; infectious diseases; autoimmune diseases; ischaemia; promotion of nerve regeneration; fibrogenetic diseases, such as, for example, sclerorma, polymyositis, systemic lupus, cirrhosis of the liver, keloid formation, interstitial nephritis and pulmonary fibrosis;

5-[4-(2-Methylphenyl)-3-hydroxy-4H-1,2,4-triazol-5-yl]-2,4-dihydroxy-N-methyl-N-butylbenzamide can inhibit, in particular, the growth of cancer, tumour cells and tumour metastases and is therefore suitable for tumour therapy.

The present invention furthermore encompasses the use of 5-[4-(2-methylphenyl)-3-hydroxy-4H-1,2,4-triazol-5-yl]-2,4-dihydroxy-N-methyl-N-butylbenzamide and/or physiologically acceptable salts and solvates thereof for the preparation of a medicament for the protection of normal cells against toxicity caused by chemotherapy, and for the treatment of diseases in which incorrect protein folding or aggregation is a principal causal factor, such as, for example, scrapie, Creutzfeldt-Jakob disease, Huntington's or Alzheimer's.

The invention also relates to the use of 5-[4-(2-methylphenyl)-3-hydroxy-4H-1,2,4-triazol-5-yl]-2,4-dihydroxy-N-methyl-N-butylbenzamide and/or physiologically acceptable salts and solvates thereof for the preparation of a medicament for the treatment of diseases of the central nervous system, of cardiovascular diseases and cachexia.

In a further embodiment, the invention also relates to the use of 5-[4-(2-methylphenyl)-3-hydroxy-4H-1,2,4-triazol-5-yl]-2,4-dihydroxy-N-methyl-N-butylbenzamide and/or physiologically acceptable salts and solvates thereof for the preparation of a medicament for HSP90 modulation, where the modulated biological HSP90 activity causes an immune reaction in an individual, protein transport from the endoplasmatic reticulum, recovery from hypoxic/anoxic stress, recovery from malnutrition, recovery from heat stress, or combinations thereof, and/or where the disorder is a type of cancer, an infectious disease, a disorder associated with disrupted protein transport from the endoplasmatic reticulum, a disorder associated with ischaemia/reperfusion, or combinations thereof, where the disorder associated with ischaemia/reperfusion is a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

In a further embodiment, the invention also relates to the use of 5-[4-(2-methylphenyl)-3-hydroxy-4H-1,2,4-triazol-5-yl]-2,4-dihydroxy-N-methyl-N-butylbenzamide and/or physiologically acceptable salts and solvates thereof for the preparation of a medicament for the treatment of ischaemia as a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

Test Method for the Measurement of HSP90 Inhibitors

The binding of geldanamycin or 17-allylamino-17-demethoxygeldanamycin (17AAG) to HSP90 and competitive inhibition thereof can be utilised in order to determine the inhibitory activity of the compounds according to the invention (Carreras et al. 2003, Chiosis et al. 2002).

In the specific case, a radioligand filter binding test is used. The radioligand used here is tritium-labelled 17-allylaminogeldanamycin, [3H]17AAG. This filter binding test allows a targeted search for inhibitors which interfere with the ATP binding site.

Material

Recombinant human HSP90α (*E. coli* expressed, 95% purity); [3H]17AAG (17-allylaminogeldanamycin, [allylamino-2,3-$^3$H. Specific activity: $1.11 \times 10^{12}$ Bq/mmol (Moravek, MT-1717);

HEPES filter buffer (50 mM HEPES, pH 7.0, 5 mM MgCl2, BSA 0.01%) Multiscreen FB (1 μm) filter plate (Millipore, MAFBNOB 50).

Method

The 96-well microtitre filter plates are firstly irrigated and coated with 0.1% of polyethylenimine.

The test is carried out under the following conditions:
Reaction temperature 22° C.
Reaction time: 30 min., shaking at 800 rpm
Test volume: 50 μl
Final concentrations:
50 mM HEPES HCl, pH 7.0, 5 mM MgCl2, 0.01% (w/v) BSA
HSP90:1.5 μg/assay
[3H]17AAG: 0.08 μM.

At the end of the reaction, the supernatant in the filter plate is removed by suction with the aid of a vacuum manifold (Multiscreen Separation System, Millipore), and the filter is washed twice.

The filter plates are then measured in a beta counter (Microbeta, Wallac) with scintillator (Microscint 20, Packard).

"% of control" is determined from the "counts per minutes" values and the $IC_{50}$ value of a compound is calculated therefrom.

The following table shows comparative measurements of the compound according to the invention with compound "A47" from the closest prior art. Compound "C1" according to the invention has an approximately 10 times higher activity in HSP90 inhibition.

Test Results

TABLE I

| HSP90 inhibition | |
|---|---|
| Compound | $IC_{50}$ [mol/l] |
| 5-[4-(2-Methylphenyl)-3-hydroxy-4H-1,2,4-triazol-5-yl]-2,4-dihydroxy-N-methyl-N-propylbenzamide ("A47") | 1.60E-07 |
| 5-[4-(2-Methylphenyl)-3-hydroxy-4H-1,2,4-triazol-5-yl]-2,4-dihydroxy-N-methyl-N-butylbenzamide ("C1") | 2.90E-08 |

Above and below, all temperatures are indicated in ° C. In the following examples, "conventional work-up" means: if necessary, water is added, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

LC-MS Conditions

HP 1100 series Hewlett Packard System having the following features: ion source: electrospray (positive mode); scan: 100-1000 m/e; fragmentation voltage: 60 V; gas temperature: 300° C., DAD: 220 nm.

Flow rate: 2.4 ml/min. The splitter used reduced the flow rate for the MS to 0.75 ml/min. after the DAD.

Column: Chromolith SpeedROD RP-18e 50-4.6

Solvent: LiChrosolv quality from Merck KGaA

Solvent A: H2O (0.01% of TFA)

Solvent B: ACN (0.008% of TFA)

Gradient:

20% of B→100% of B: 0 min to 2.8 min

100% of B: 2.8 min to 3.3 min

100% of B 20% of B: 3.3 min to 4 min

The retention times $R_f$ or $R_t$ [min] and M+H$^+$ data MW indicated in the following examples are the measurement results of the LC-MS measurements.

REFERENCE EXAMPLE 1

Preparation of 5-(2,4-dihydroxy-5-phenethylphenyl)-4-(2-fluorophenyl)-3-hydroxy-4H-1,2,4-triazole ("A1"):

1.1 A solution of 15 g of 5-bromo-2,4-dihydroxybenzoic acid, 14.4 ml of iodomethane and 62.9 g of caesium carbonate in 100 ml of N,N-dimethylformamide (DMF) is heated under reflux for 16 hours. The mixture is subjected to conventional work-up, giving 16.7 g of 5-bromo-2,4-dimethoxybenzoic acid ("1").

1.2 A mixture of 4 g of "1" and 2 drops of DMF in 40 ml of thionyl chloride is stirred at room temperature for 16 hours. Removal of the solvent gives 4.3 g of 5-bromo-2,4-dimethoxybenzoyl chloride ("2"), $R_f$ 1.610; MW 280.5. The product is reacted without further purification.

1.3 A solution of 3.8 g of "2" in 25 ml of dichloromethane is added dropwise with ice-cooling to a solution of 1.314 ml of 2-fluoroaniline and 1.13 ml of pyridine in 25 ml of dichloromethane, and the mixture is stirred at room temperature for 5 hours. Conventional work-up and crystallisation from isopropanol gives 4.5 g of 5-bromo-N-(2-fluorophenyl)-2,4-dimethoxybenzamide ("3"), $R_f$ 2.217; MW 355.2.

1.4 2.9 g of PCl$_5$ are added under a nitrogen atmosphere to a solution of 4.5 g of "3" in 60 ml of toluene, and the mixture is heated under reflux for 3 hours. The solvent is removed, the residue is dissolved in 100 ml of THF, and the solution is added dropwise at 0° to 138 ml of a 1 M hydrazine solution in THF. The mixture is stirred for a further 16 hours, subjected to conventional work-up and crystallised from isopropanol, giving 3.6 g of N-(2-fluorophenyl)-3-bromo-4,6-dimethoxybenzamide hydrazone ("4"), $R_f$ 0.952; MW 369.2

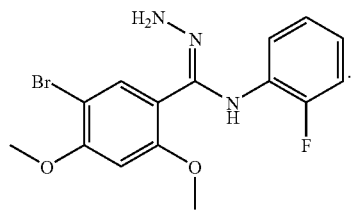

("4")

1.5 1.86 g of 1,1'-carbonyldiimidazole ("5") are added to a solution of 3.6 g of "4" in 300 ml of THF, and the mixture is stirred for a further 16 hours. The mixture is subjected to conventional work-up, the residue is boiled up with MTB ether and cooled, and the crystals are separated off, giving 700 mg of 5-(2,4-dimethoxy-5-bromophenyl)-4-(2-fluorophenyl)-3-hydroxy-4H-1,2,4-triazole ("6"), $R_f$ 1.413; MW 395.2.

1.6 600 mg of "6", 178.4 µl of styrene (stabilised), 430.2 µl of triethylamine, 14.1 mg of palladium(II) acetate (47% of Pd), 19.17 mg of tri-o-tolylphosphine and 4 ml of acetonitrile are introduced into a 10 ml vial. The mixture is irradiated for 30 minutes at 170° in the microwave. A little catalyst is added, and the mixture is irradiated a further twice. Toluene is added to the mixture, which is then extracted a number of times with water. The organic phase is dried and evaporated. The residue is purified via RP chromatography, giving 140 mg of "7", $R_f$ 1.765; MW 418.4, and 40 mg of "8"

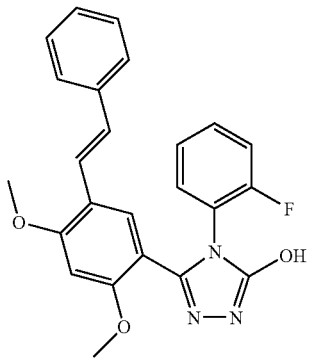

"7"

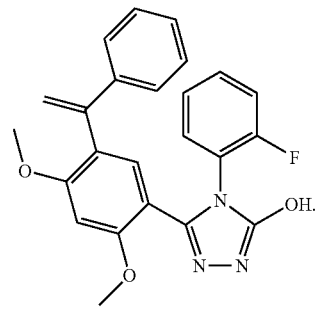

"8"

1.7 140 mg of "7" are hydrogenated under standard conditions in 10 ml of THF in the presence of 0.14 g of Pt/C (5%). The catalyst is subsequently separated off and subjected to conventional work-up, giving 140 mg of "9", $R_f$ 1.920, MW 420.5

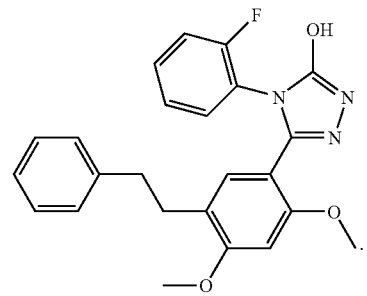

"9"

1.8 158.5 µl of boron tribromide are added at −10° to a solution of 140 mg of "9" in 2 ml of dichloromethane, and the mixture is stirred at room temperature for a further 16 hours. Methanol is added at 0°, the solvents are separated off, and the residue is purified via RP chromatography, giving 74 mg of "A1", $R_f$ 1.537; MW 392.4, and 27 mg of "A2", $R_f$ 1.884; MW 398.4

2.3 55 mg of 5-[4-(2-fluorophenyl)-3-hydroxy-4H-1,2,4-triazol-5-yl]-2,4-dihydroxybenzoic acid, 2 mole-equivalents of t-butyldimethylchlorosilane and 3 mole-equivalents of imidazole in 2 ml of THF are stirred at room temperature for 3 h, giving

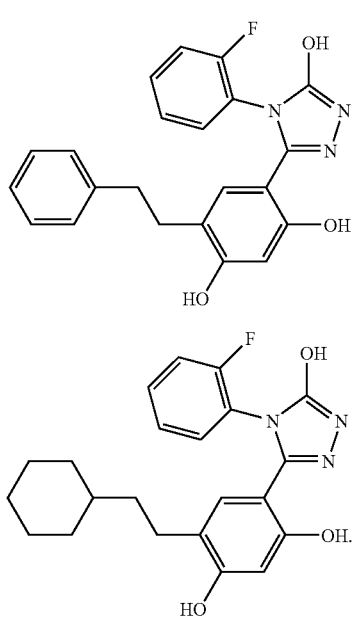

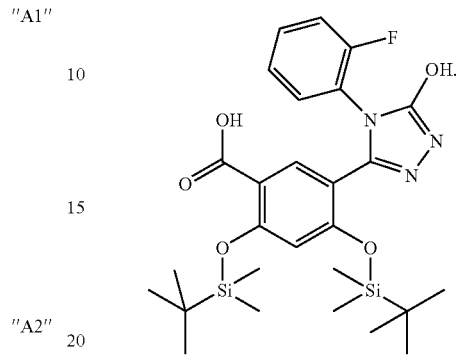

2.4 The product obtained in 2.3 is dissolved in 1.5 ml of THF, and 2 eq. of 1-(3-dimethylaminopropyl)-3-ethylcarbodiimide hydrochloride are added. After 1 h at room temperature, 1.2 eq. of propylmethylamine are added, and the mixture is stirred for a further 18 h. 3 eq. of tetramethylammonium fluoride are subsequently added, and the mixture is stirred at room temperature for 2 h. After concentration, the product is separated off, giving 42 mg of "A46"; $R_t$ 1.139 min, m/e 387; MW 386

REFERENCE EXAMPLE 2

Preparation of 5-[4-(2-fluorophenyl)-3-hydroxy-4H-1,2,4-triazol-5-yl]-2,4-dihydroxy-N-methyl-N-propylbenzamide ("A46")

2.1 A solution of 100 mg of 5-(2,4-dimethoxy-5-bromophenyl)-4-(2-fluorophenyl)-3-hydroxy-4H-1,2,4-triazole ("6"), 7 mg of [(R)-(+)-2,2'-bis(diphenylphosphino)-1,1'-binaphthyl]palladium(II) chloride, 5.7 ml of carbon monoxide and 35 µl of triethylamine in 20 ml of methanol is treated at 100° C. and 7.5 bar for 20 h in an autoclave. The resultant solution is subsequently concentrated and crystallised from ethanol, giving 91 mg of methyl 5-[4-(2-fluorophenyl)-3-hydroxy-4H-1,2,4-triazol-5-yl]-2,4-dimethoxybenzoate

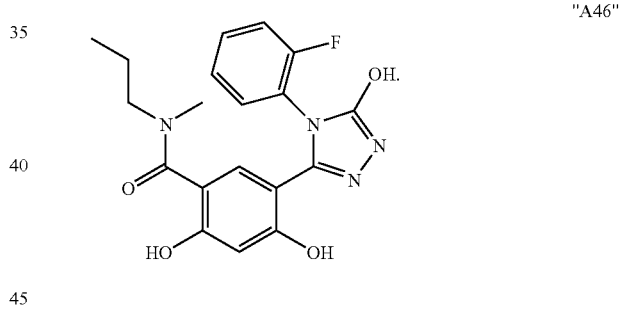

The following compound is obtained analogously:
5-[4-(2-methylphenyl)-3-hydroxy-4H-1,2,4-triazol-5-yl]-2,4-dihydroxy-N-methyl-N-propylbenzamide ("A47"), MW 383.4.

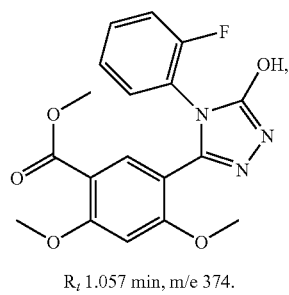

$R_t$ 1.057 min, m/e 374.

2.2 Analogously to Example 1.8, reaction of 90 mg of methyl 5-[4-(2-fluorophenyl)-3-hydroxy-4H-1,2,4-triazol-5-yl]-2,4-dimethoxybenzoate gives 57.2 mg of the compound 5-[4-(2-fluorophenyl)-3-hydroxy-4H-1,2,4-triazol-5-yl]-2,4-dihydroxybenzoic acid, $R_t$ 0.598 min, m/e 332.

EXAMPLE 1

The compound according to the invention 5-[4-(2-methylphenyl)-3-hydroxy-4H-1,2,4-triazol-5-yl]-2,4-dihydroxy-N-methyl-N-butylbenzamide ("C1") is obtained analogously to the preparation of "A47";

$^1$H NMR (500 MHz, DMSO-$d_6$) δ 11.86 (s, 1H), 9.92 (s, 1H), 7.28-7.23 (m, 2H), 7.14-7.10 (m, 1H), 7.03-7.01 (m, 1H), 6.88 (s, 1H), 6.26 (s, 1H), 3.16 (broad m, 2H), 2.73 (broad s, 3H), 2.14 (s, 3H), 1.40 (broad m, 2H), 1.15 (broad m, 2H), 0.81 (broad m, 3H).

EXAMPLE 2

The synthesis of "C1" can be carried out as follows:

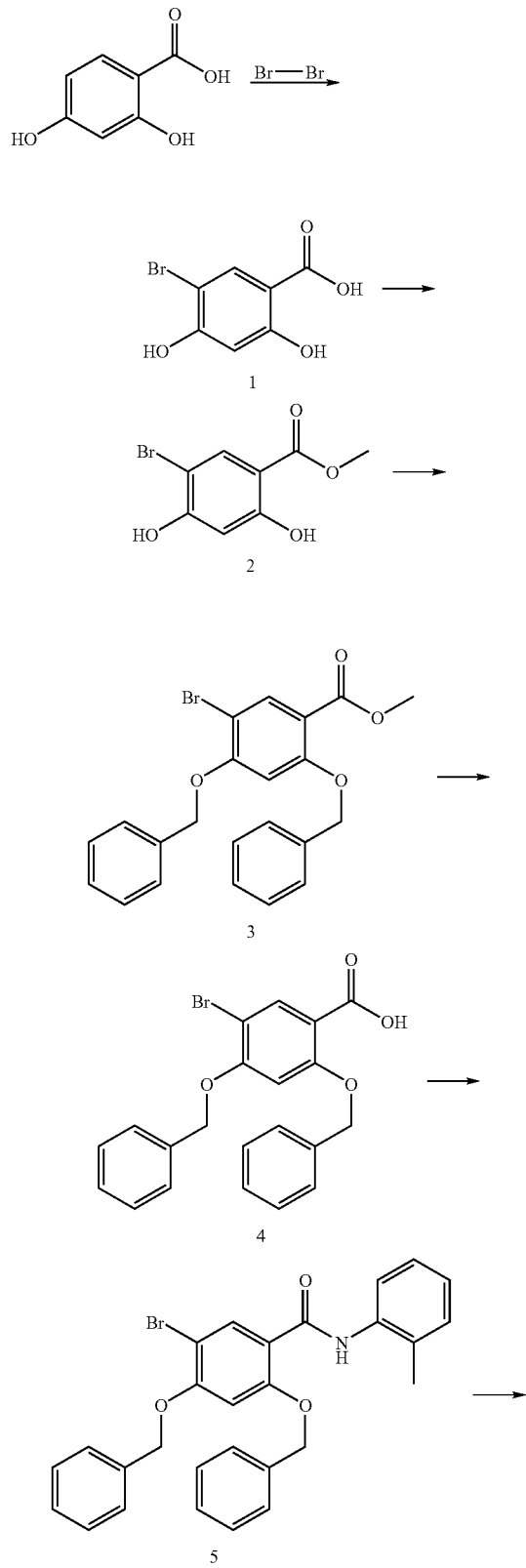

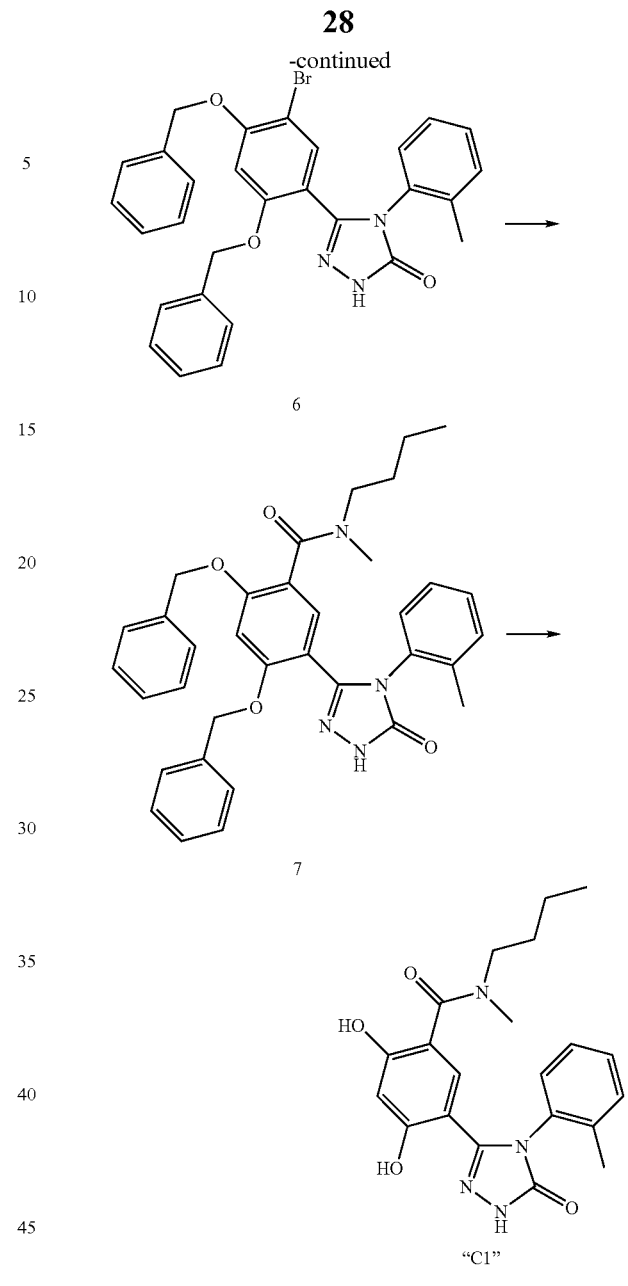

2.1 5-Bromo-2,4-dihydroxybenzoic acid (1)

3.55 kg of 2,4-dihydroxybenzoic acid are dissolved in 30 l of glacial acetic acid. A solution of 1060 ml of bromine in 10 l of glacial acetic acid is subsequently added dropwise at 15° C. over a period of 8 h. Stirring is then continued at 20° C. for 16 h, the mixture is evaporated in vacuo, and the crystalline residue is slurried in 20 l of dichloromethane and stirred for 1 h. Filtration and drying in air gives 4.9 kg of white crude product. Recrystallisation from 30 l of toluene/acetonitrile (1:1) and drying gives 3.549 kg (66% yield) of 5-bromo-2,4-dihydroxybenzoic acid (m.p. 210-211.5° C.; MW 233.0).

2.2 Methyl 5-bromo-2,4-dihydroxybenzoate (2)

8.9 kg of 5-bromo-2,4-dihydroxybenzoic acid are dissolved in 70 l of methanol and heated to 55° C. 800 ml of sulfuric acid (w=95-98%) are subsequently metered in, and the mixture is stirred under gentle reflux for 4 days, with a further 500 ml of sulfuric acid (w=95-98%) being added daily (3 times). The reaction mixture is stirred into a cooled solution (5° C.) of 9 kg of sodium hydrogencarbonate in 100 l of water. Filtration and drying in vacuo at 50° C. gives 7.87 kg (83%) of methyl 5-bromo-2,4-dihydroxybenzoate (white crystals), MW 247.1.

2.3 Methyl 2,4-bisbenzyloxy-5-bromobenzoate (3)

7.86 kg (83%) of methyl 5-bromo-2,4-dihydroxybenzoate and 9.65 kg of potassium carbonate are suspended in 100 l of acetonitrile at 0° C. The mixture is subsequently heated to 80° C., and 7575 ml of benzyl bromide are added via a dropping funnel over a period of 40 min. After stirring at 80° C. for 16 h, the mixture is filtered, and the collected filtrate is evaporated in vacuo: 12.95 kg (95%) of methyl 2,4-bisbenzyloxy-5-bromobenzoate (slightly yellow crystals); MW 427.3.

2.4 2,4-Bisbenzyloxy-5-bromobenzoic acid (4)

6.4 kg of methyl 2,4-bisbenzyloxy-5-bromobenzoate in 18 l of THF are added to a solution of 3 kg of sodium hydroxide in 30 l of water. After stirring overnight at 68° C., the mixture is cooled to 10° C., and 7.5 l of HCl (w: 37%) are added via a dropping funnel (pH 1). The mixture is stirred for a further 1 h and subsequently filtered. The residue is dried to constant weight in vacuo at 60° C.; 5.687 kg (91%) of 2,4-bisbenzyloxy-5-bromo-benzoic acid (m.p. 150-152° C.; MW 413.3).

2.5 2,4-Bisbenzyloxy-5-bromo-N-o-tolylbenzamide (5)

80 ml of DMF are added to 42 l of thionyl chloride. The mixture is cooled to 2-9° C., and 11.55 kg of 2,4-bisbenzyloxy-5-bromobenzoic acid are added over a period of 1 h. Stirring is continued at this temperature for a further 1 h and then at 25° C. for 16 h. Thionyl chloride is then distilled off in vacuo (300 mbar, 46° C.). 3 l of toluene are added to the resultant residue, and the mixture is again evaporated to dryness, and this procedure is repeated a further twice. The resultant product is employed for the following reaction without further purification. 13.6 kg (plus toluene).

2.8 l of o-toluidine and 2.5 l of pyridine are added to 50 l of dichloromethane at 3° C. 13.6 kg of 2,4-bisbenzyloxy-5-bromobenzoyl chloride (toluene-moist) suspended in 35 l of dichloromethane are added to this solution over the course of 2 h. The mixture is subsequently stirred overnight at 23° C., and the solid is filtered off and rinsed with dichloromethane (2× with 5 l each time). The crude product obtained in this way (8 kg) is dissolved in 40 l of dichloromethane and extracted successively with 40 l of distilled water, 50 l of hydrochloric acid (~1 mol/l; prepared from 5 l of HCl w: 37% and 50 l of water). The organic phase is subsequently washed with 50 l of water. The organic phase is dried for 3 days using 6 kg of sodium sulfate. The drying agent is filtered off with suction via a suction filter, and the filtrate is evaporated to dryness in a rotary evaporator. Recrystallisation from ethanol (35 l, 65° C.) and drying (50° C./35 mbar) to constant weight gives 10.84 kg (82%) of 2,4-bisbenzyloxy-5-bromo-N-o-tolylbenzamide (m.p. 174.5° C.-176° C.; MW 502.4).

2.6 5-(2,4-Bisbenzyloxy-5-bromophenyl)-4-(2-methylphenyl)-3-hydroxy-4H-1,2,4-triazole (6)

1.75 kg of phosphorus pentachloride are added at 3° C. to 3.5 kg of 2,4-bisbenzyloxy-5-bromo-N-o-tolylbenzamide in 60 l of toluene. The mixture is subsequently heated at 135° C. for 4 h, and stirring is then continued at 25° C. for 16 h. Evaporation in vacuo gives 3.6 kg of crystalline material. The latter is taken up in 18 l of THF and added to a solution of 1.38 kg of Boc-hydrazine in 30 l of THF at 3° C. over the course of 1.5 h. After warming to 25° C. and stirring for 16 h, the product is filtered off with suction (4.3 kg of white product—THF-moist) and employed directly in the following reaction.

The product is dissolved in 30 l of THF, and 7 l of hydrochloric acid (w: 37%) are added at 1° C. over the course of 20 min. The mixture is stirred at 23° C. for 16 h and cooled to −5° C., and 7.5 l of sodium hydroxide solution (w: 32%) are added dropwise over the course of 1.5 h. The phases are separated, and the organic phase is washed with 25 l of saturated sodium chloride solution (prepared from 8.75 kg of sodium chloride and 25 l of water). The organic phase is dried using 6 kg of sodium sulfate, the drying agent is filtered off with suction, and the filtrate is evaporated to dryness in a rotary evaporator. 2×5 l of toluene are added to the residue, and a "sharp" distillation is carried out in order to "entrain" remaining water. The residue obtained in this way is reacted further directly.

1.3 kg of carbonyldiimidazole (CDI) are dissolved in 100 l of THF. After cooling to 3° C., the product from the preceding reaction is slowly added dropwise to 25 l of THF. The mixture is subsequently stirred at 25° C. for 16 h and extracted with 30 l of saturated sodium chloride solution, and the organic phase is then extracted with 25 l of 1N HCl. The organic phase is subsequently washed with 25 l of saturated sodium chloride solution and dried using 10 kg of sodium sulfate. Filtration and evaporation of the organic phase in vacuo gives a solid residue, which is taken up in 5 l of toluene and again evaporated to dryness in vacuo. Recrystallisation from 20 l of 2-propanol at 70° C. gives 2.7 kg (76%) of 5-(2,4-bisbenzyloxy-5-bromophenyl)-4-(2-methylphenyl)-3-hydroxy-4H-1,2,4-triazole, MW 542.4.

2.7 5-[4-(2-Methylphenyl)-3-hydroxy-4H-1,2,4-triazol-5-yl]-2,4-bisbenzyloxy-N-methyl-N-butylbenzamide (7)

A solution of 2 kg of 5-(2,4-bisbenzyloxy-5-bromophenyl)-4-(2-methylphenyl)-3-hydroxy-4H-1,2,4-triazole, 90 g of (1,1'-bis(diphenylphosphino)ferrocene)palladium(II) chloride, 83 l of carbon monoxide, 479 g of triethylamine and 400 g of N-methylbutylamine in 25 l of THF is treated at 120° C. and 5-10 bar for 20 h in an autoclave. The resultant solution is subsequently evaporated and crystallised from ethanol, giving 1.4 kg (70%) of 5-[4-(2-methylphenyl)-3-hydroxy-4H-1,2,4-triazol-5-yl]-2,4-bis-benzyloxy-N-methyl-N-butylbenzamide, MW 476.7.

2.8 5-[4-(2-Methylphenyl)-3-hydroxy-4H-1,2,4-triazol-5-yl]-2,4-dihydroxy-N-methyl-N-butylbenzamide ("A1")

A solution of 1.1 kg of 5-[4-(2-methylphenyl)-3-hydroxy-4H-1,2,4-triazol-5-yl]-2,4-bisbenzyloxy-N-methyl-N-butylbenzamide, 5% Pd/C (50.5% of water) and 85 l of hydrogen in 10 l of THF is treated at 23° C. for 7 h in an autoclave. The resultant solution is subsequently evaporated and crystallised from ethanol, giving 738 g (95%) of 5-[4-(2-methylphenyl)-3-hydroxy-4H-1,2,4-triazol-5-yl]-2,4-dihydroxy-N-methyl-N-butylbenzamide ("C1"); MW 396.5.

Two polymorphic forms A1 and A2 of the compound "C1" according to the invention can be isolated.

Melting Points:
Form A1: m.p. 238.5±0.1° C. (n=6)
Form A2: m.p. 209.6±0.2° C. (n=6)

Form A1 is the thermodynamically more stable form.

Powder X-ray diffractometry spectra of the two polymorphic forms are shown in FIG. 1.

Form A2 can be converted into A1, for example by stirring in solvents such as methanol, ethanol, acetone, DMF, acetic acid, formic acid, THF or isopropanol.

Powder XRD spectral data of the polymorphs A1 and A2: 10 characteristic peaks were in each case used for the evaluation.

| Sample | XRD raw data |
|---|---|
| Batch 7, form A1 | RT 162-07 |
| Batch 12, form A2 | RT 2214-07 |

Procedure and Results:
X-Ray Powder Diffraction (XRD)
All samples were measured by XRD
RT 162-07:
  D5000 diffractometer [Bruker AXS]
  Transmission mode
  Generator power 30 kV/40 mA
  CuKα1-radiation 1.5406 Å (primary monochromator)
  Position sensitive detector
XRD Measurement Conditions:
Range: 3-65°2θ
Resolution: 0.05°2θ
Step time: 1.4 s
RT 2214-07:
  Stoe Powder-X-ray-diffractometer system STADIP 611 KL
  Transmission mode
  Generator power 40 kV/40 mA
  Cu-Kα1 radiation 1.5406 Å (primary monochromator)
  Position-sensitive detector
XRD Measurement Conditions:
Range: 3-65°2θ
Resolution: 0.5°2θ
Step time: 15 s
Form A1; RT 162-07:

| No. | d [Å] | 2θ | I/Io |
|---|---|---|---|
| 1 | 9.3 | 9.5 | 100 |
| 2 | 6.8 | 13.0 | 43 |
| 3 | 5.3 | 16.8 | 60 |
| 4 | 4.7 | 18.9 | 50 |
| 5 | 4.6 | 19.5 | 75 |
| 6 | 4.1 | 21.8 | 15 |
| 7 | 3.6 | 24.7 | 96 |
| 8 | 3.4 | 26.4 | 21 |
| 9 | 3.2 | 27.8 | 16 |
| 10 | 2.5 | 36.6 | 11 |

Form A2; RT 2214-07:

| No. | d [Å] | 2θ | I/Io |
|---|---|---|---|
| 1 | 11.8 | 7.5 | 38 |
| 2 | 8.4 | 10.5 | 100 |
| 3 | 5.4 | 16.4 | 32 |
| 4 | 4.4 | 20.2 | 60 |
| 5 | 4.2 | 20.9 | 64 |
| 6 | 4.0 | 22.4 | 46 |
| 7 | 3.8 | 23.5 | 28 |
| 8 | 2.9 | 31.2 | 11 |
| 9 | 2.3 | 38.8 | 13 |
| 10 | 2.2 | 41.3 | 9 |

Preparation of Prodrug Compounds

EXAMPLE 3

Preparation of mono-[2-(butylmethylcarbamoyl)-5-hydroxy-4-(5-oxo-4-o-tolyl-4,5-dihydro-1H-1,2,4-triazol-3-yl)phenyl]phosphate

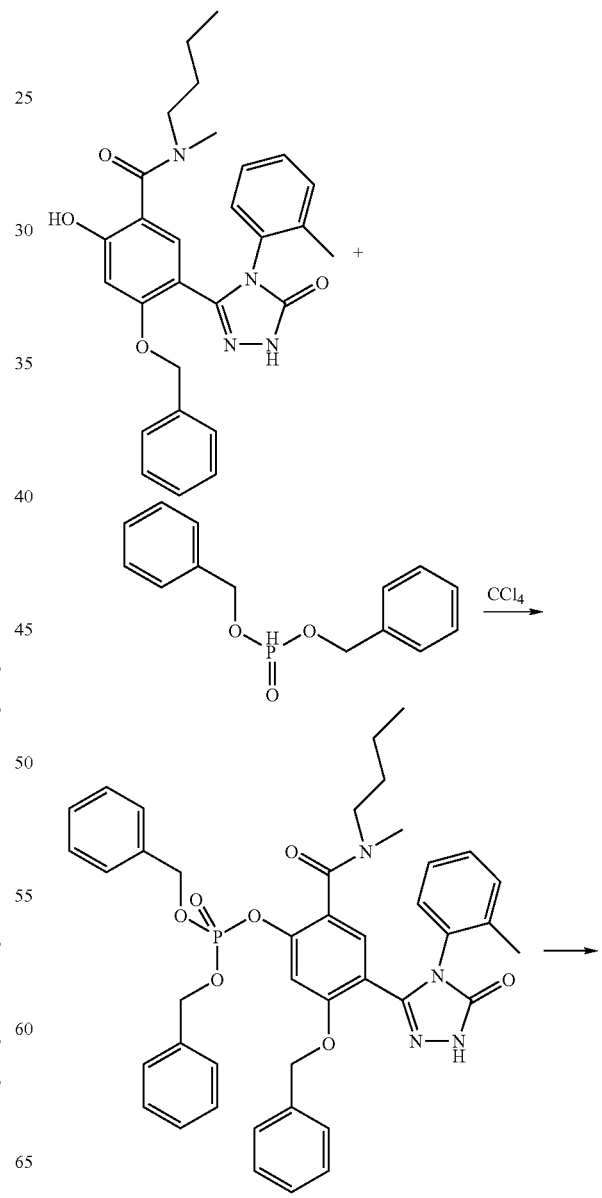

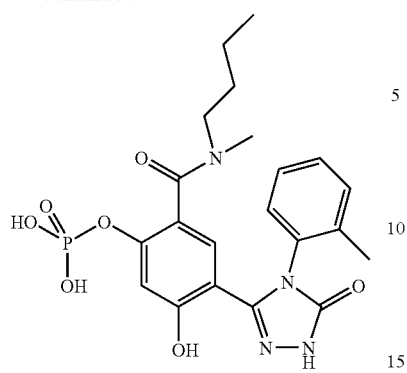

700 mg of 5-[4-(2-methylphenyl)-3-hydroxy-4H-1,2,4-triazol-5-yl]-4-benzyloxy-2-hydroxy-N-methyl-N-butyl-benzamide are initially introduced in 20 ml of acetonitrile with cooling, and 10 ml of carbon tetrachloride are added. 0.5 ml of N-ethyldiisopropylamine and 50 mg of 4-(dimethylamino)pyridine and, slowly at −10° C., 326 μl of dibenzyl phosphonite are then added dropwise. The mixture is stirred at this temperature for a further 30 min, 10 ml of a 0.5 M $KH_2PO_4$ solution in water are added, and the mixture is extracted with ethyl ether, dried over sodium sulfate, filtered and evaporated. Column chromatography gives 550 mg (51%) of 5-[4-(2-methylphenyl)-3-hydroxy-4H-1,2,4-triazol-5-yl]-4-benzyloxy-2-(dibenzyl phosphate)-N-methyl-N-butylbenzamide (Rf 2.196 min; MW 746.8).

A solution of 550 mg of 5-[4-(2-methylphenyl)-3-hydroxy-4H-1,2,4-triazol-5-yl]-4-benzyloxy-2-(dibenzyl phosphite)-N-methyl-N-butylbenzamide, 5% Pd/C (50.5% of water) and 49.5 ml of hydrogen in 10 ml of THF is treated at 23° C. for 19 h in an autoclave. The resultant solution is subsequently evaporated and crystallised from ethyl ether; 280 mg (79.8%) of mono-[2-(butylmethylcarbamoyl)-5-hydroxy-4-(5-oxo-4-o-tolyl-4,5-dihydro-1H-1,2,4-triazol-3-yl)phenyl]phosphate (Rf 0.645 min; MW 476.4).

EXAMPLE 4

Preparation of mono-[4-(butylmethylcarbamoyl)-2-(5-oxo-4-o-tolyl-4,5-dihydro-1H-1,2,4-triazol-3-yl)-5-phosphonooxyphenyl]phosphate (E)

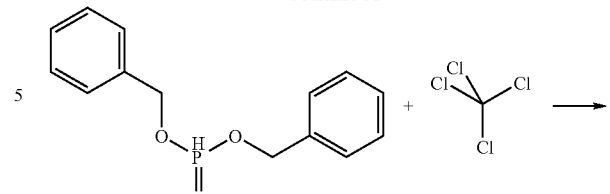

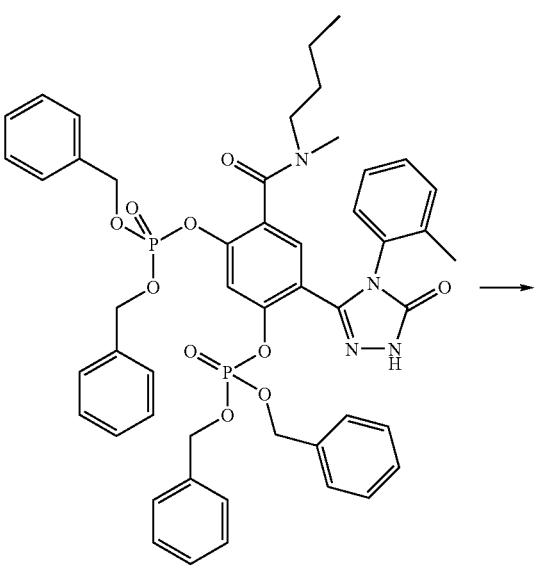

D

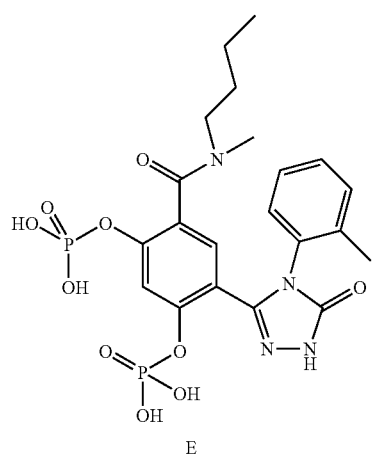

E

The synthesis is carried out analogously to Example 3; D: MW 916; Rf 2.335 min E: MW 556.4; Rf 0.883 min.

EXAMPLE 5
Preparation of mono-[4-(butylmethylcarbamoyl)-5-hydroxy-2-(5-oxo-4-o-tolyl-4,5-dihydro-1H-1,2,4-triazol-3-yl)phenyl]phosphate (F)
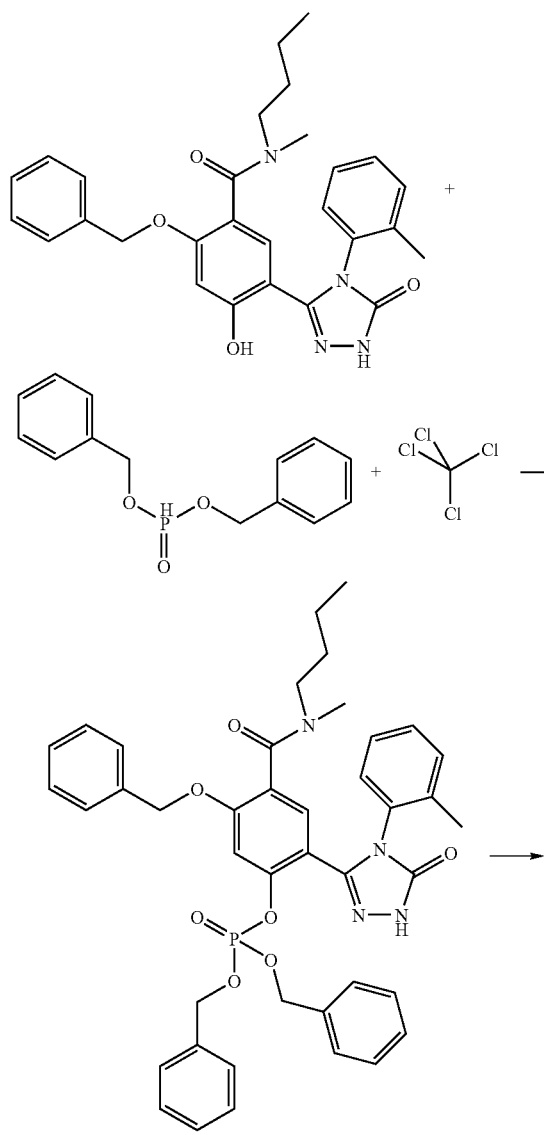
The synthesis is carried out analogously to Example 3:
F: MW 476.4; Rf 1.321 min.
EXAMPLE 6
Preparation of N-butyl-2,4-dihydroxy-N-methyl-5-(5-thioxo-4-o-tolyl-4,5-dihydro-1H-1,2,4-triazol-3-yl)benzamide (G)
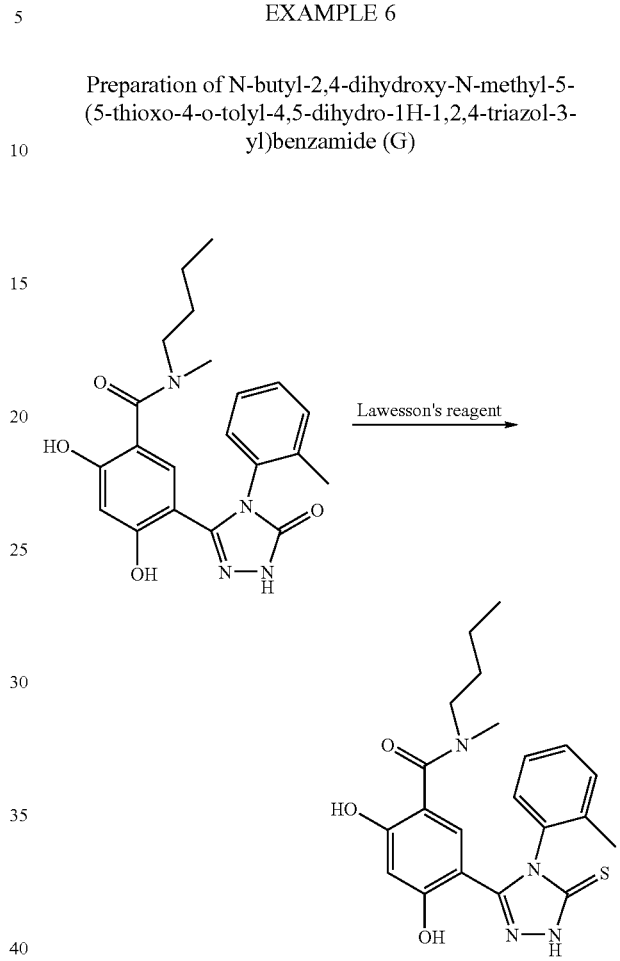
EXAMPLE 7
Preparation of glucuronic acid derivatives of "C1"
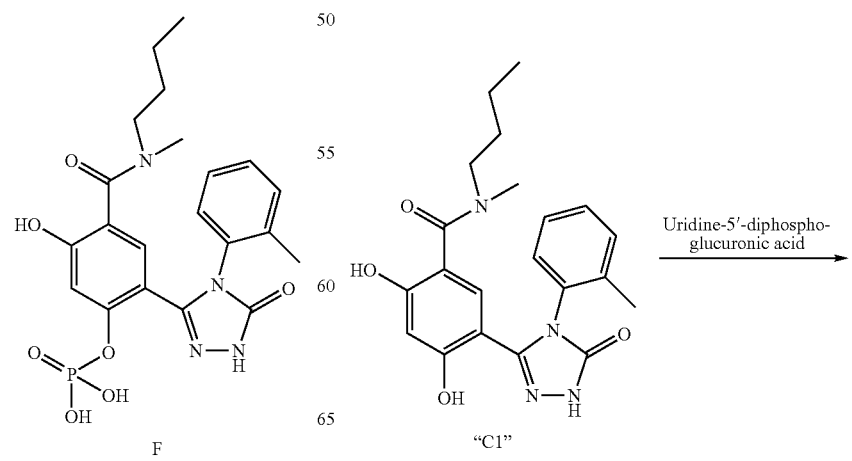

-continued

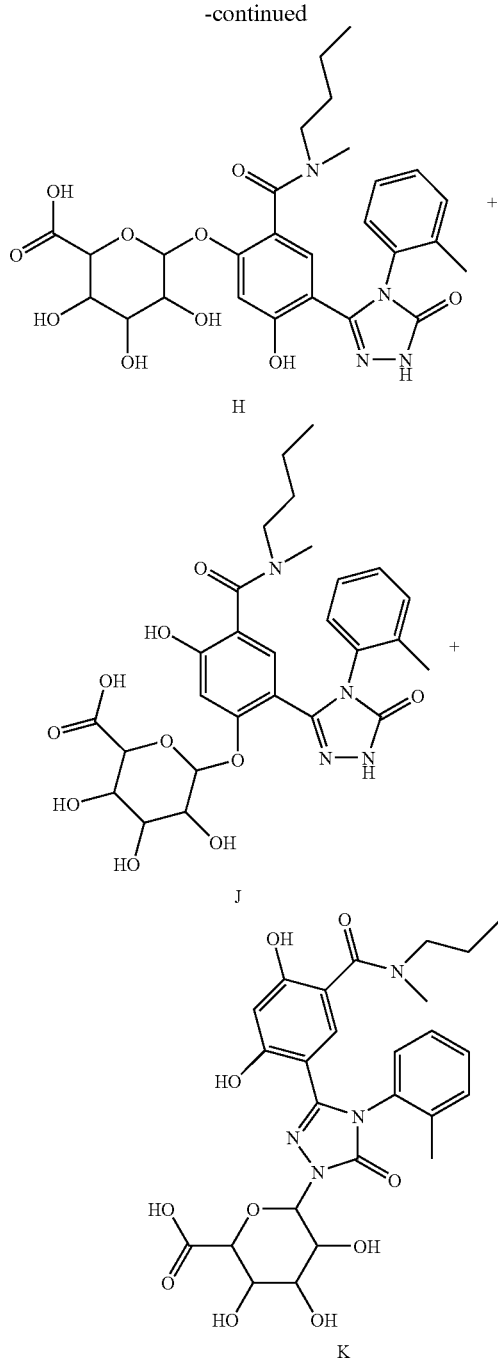

H

J

K 4 ml of potassium phosphate buffer (0.1 M/pH 7.4 with 1.0 mM $MgCl_2$), 100 mg of uridine-5'-diphosphoglucuronic acid sodium salt, 10 mg of "C1" (suspended in 1 ml of 20% acetonitrile) and 1 ml of pig liver homogenate are introduced into a sample vial. The batch is incubated at 37°.

After 24 h, acetonitrile is added, the mixture is centrifuged, and the supernatants are then evaporated to dryness.

Separation and analysis of the three regioisomers is carried out by means of LC-MS.

LC-MS Conditions

Hewlett Packard HP 1100 series system with the following features: ion source: electrospray (positive mode); scan: 100-1000 m/e;
Fragmentation voltage: 60 V;
Gas temperature: 300° C.;
DAD: 220 nm.
Flow rate: 2.4 ml/min. The splitter used reduces the flow rate for the MS to 0.75 ml/min after the DAD.
Column: Chromolith SpeedROD RP-18e 50-4.6
Solvent: LiChrosolv grade from Merck KGaA
Solvent A: $H_2O$ (0.01% of TFA)
Solvent B: acetonitrile (0.008% of TFA)
Polar gradient:
5% of B →100% of B: 0 min to 3.0 min
100% of B: 3.0 min to 3.3 min
100% of B →20% of B: 3.3 min to 4 min.

For three compounds of equal mass, the following $R_T$ values are found: 1.307, 1.406 and 1.465 min.

Isomer H was unambiguously identified by NMR spectroscopy.

The one-dimensional $^1$H-NMR spectrum and two-dimensional HSQC, HMBC and ROESY spectra were obtained under the following conditions:

Bruker DRX 500 spectrometer; DMSO-$d_6$, 303 K, TMS as standard.

Assignment of the $^1$H-NMR spectrum:

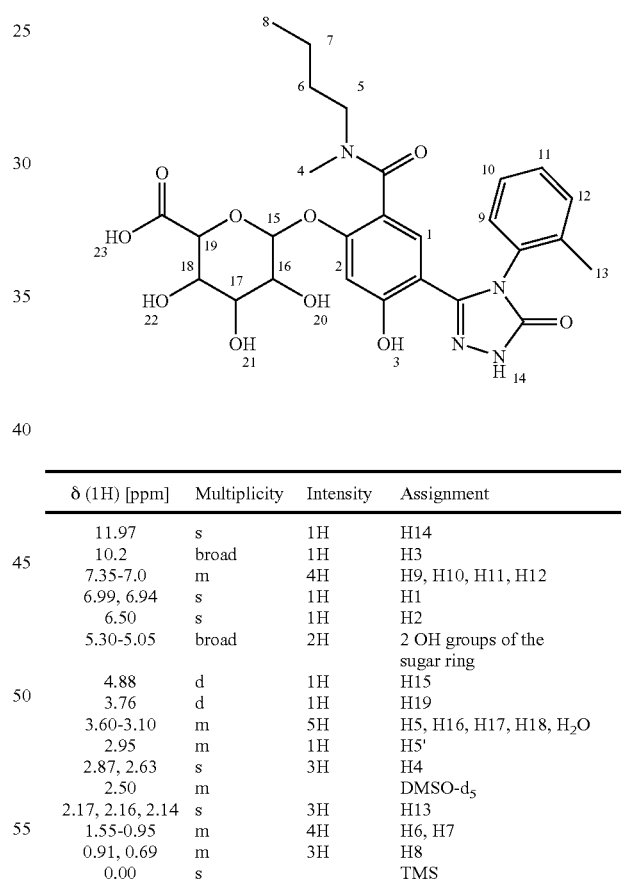

| δ (1H) [ppm] | Multiplicity | Intensity | Assignment |
|---|---|---|---|
| 11.97 | s | 1H | H14 |
| 10.2 | broad | 1H | H3 |
| 7.35-7.0 | m | 4H | H9, H10, H11, H12 |
| 6.99, 6.94 | s | 1H | H1 |
| 6.50 | s | 1H | H2 |
| 5.30-5.05 | broad | 2H | 2 OH groups of the sugar ring |
| 4.88 | d | 1H | H15 |
| 3.76 | d | 1H | H19 |
| 3.60-3.10 | m | 5H | H5, H16, H17, H18, $H_2O$ |
| 2.95 | m | 1H | H5' |
| 2.87, 2.63 | s | 3H | H4 |
| 2.50 | m | | DMSO-$d_5$ |
| 2.17, 2.16, 2.14 | s | 3H | H13 |
| 1.55-0.95 | m | 4H | H6, H7 |
| 0.91, 0.69 | m | 3H | H8 |
| 0.00 | s | | TMS |

The following examples relate to pharmaceutical compositions:

EXAMPLE A

Injection vials

A solution of 100 g of the active ingredient according to the invention and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of the active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of the active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of the active ingredient according to the invention are mixed with 99.5 g of Vaseline under aseptic conditions.

EXAMPLE E

Tablets

A mixture of 1 kg of active ingredient according to the invention, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient according to the invention are introduced into hard gelatine capsules in a conventional manner in such a way that each capsule contains 20 mg of the active ingredient.

EXAMPLE H

Ampoules

A solution of 1 kg of the active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:

1. The compound 5-[4-(2-methylphenyl)-3-hydroxy-4H-1,2,4-triazol-5-yl]-2,4-dihydroxy-N-methyl-N-butylbenzamide,
   or a pharmaceutically acceptable derivative thereof, which is a mono- or diphos-phoric acid derivative, thioxo derivative, or mono- or diglucuronic acid derivative thereof,
   or a salt thereof,
   or a mono- or di-hydrate or alcoholate thereof,
   or tautomer thereof,
   or stereoisomer thereof.

2. A compound according to claim 1, which is the mono- or diphosphoric acid derivative, thioxo derivative, or mono- or diglucuronic acid derivative thereof.

3. A pharmaceutical composition comprising 5-[4-(2-methylphenyl)-3-hydroxy-4H-1,2,4-triazol-5-yl]-2,4-dihydroxy-N-methyl-N-butylbenzamide
   or a pharmaceutically acceptable derivative thereof, which is a mono- or diphosphoric acid derivative, thioxo derivative, or mono- or diglucuronic acid derivative thereof,
   or a salt thereof,
   or a mono- or di-hydrate or alcoholate thereof,
   or tautomer thereof,
   or stereoisomer thereof
   and one or more pharmaceutically acceptable excipients and/or adjuvants.

4. A pharmaceutical composition according to claim 3, which comprises a further pharmaceutically active ingredient.

5. A kit containing separate packs of
   (a) an effective amount of 5-[4-(2-methylphenyl)-3-hydroxy-4H-1,2,4-triazol-5-yl]-2,4-dihydroxy-N-methyl-N-butylbenzamide
   or a pharmaceutically acceptable derivative thereof, which is a mono- or diphosphoric acid derivative, thioxo derivative, or mono- or diglucuronic acid derivative thereof,
   or a salt thereof,
   or a mono- or di-hydrate or alcoholate thereof,
   or tautomer thereof,
   or stereoisomer thereof, and
   (b) an effective amount of a further pharmaceutically active ingredient.

6. The compound 5-[4-(2-methylphenyl)-3-hydroxy-4H-1,2,4-triazol-5-yl]-2,4-dihydroxy-N-methyl-N-butylbenzamide according to claim 1, or a salt thereof.

7. The compound 5-[4-(2-methylphenyl)-3-hydroxy-4H-1,2,4-triazol-5-yl]-2,4-dihydroxy-N-methyl-N-butylbenzamide according to claim 1.

* * * * *